(12) United States Patent
Vilsmeier

(10) Patent No.: US 9,298,880 B2
(45) Date of Patent: Mar. 29, 2016

(54) AUTOMATIC TREATMENT PLANNING METHOD

(75) Inventor: Stefan Vilsmeier, Munich (DE)

(73) Assignee: Brainlab AG, Feldkirchen (DE)

( * ) Notice: Subject to any disclaimer, the term of this patent is extended or adjusted under 35 U.S.C. 154(b) by 464 days.

(21) Appl. No.: 13/616,092

(22) Filed: Sep. 14, 2012

(65) Prior Publication Data

US 2013/0085314 A1    Apr. 4, 2013

Related U.S. Application Data

(60) Provisional application No. 61/541,415, filed on Sep. 30, 2011.

(51) Int. Cl.
*A61N 5/00* (2006.01)
*G06F 19/00* (2011.01)
*A61N 5/10* (2006.01)

(52) U.S. Cl.
CPC ............ *G06F 19/325* (2013.01); *A61N 5/1037* (2013.01); *A61N 5/1038* (2013.01); *G06F 19/345* (2013.01); *A61N 2005/1041* (2013.01)

(58) Field of Classification Search
CPC .............. A61N 5/1038; A61N 2005/1041; A61N 5/1037; G06F 19/325; G06F 19/345
USPC ........... 600/1, 2; 128/897–899; 378/158, 156, 378/65, 87
See application file for complete search history.

(56) References Cited

U.S. PATENT DOCUMENTS

| 2007/0156453 | A1 | 7/2007 | Frielinghaus et al. |
| 2008/0039713 | A1* | 2/2008 | Thomson et al. ............. 600/411 |
| 2008/0292158 | A1* | 11/2008 | Rietzel ............ 382/128 |
| 2010/0160836 | A1* | 6/2010 | Berlinger ..................... 600/595 |
| 2010/0208867 | A1 | 8/2010 | Nord et al. |
| 2011/0046979 | A1* | 2/2011 | Tulipano et al. .................. 705/2 |
| 2013/0272593 | A1* | 10/2013 | Lee et al. ..................... 382/131 |

FOREIGN PATENT DOCUMENTS

| EP | 08 169 422.6 | 5/2010 |
| EP | 09 160 153.4 | 5/2010 |
| WO | 2007/060187 A1 | 5/2007 |
| WO | 2009/136354 A1 | 11/2009 |
| WO | 2012/085722 A1 | 6/2012 |

OTHER PUBLICATIONS

Extended European Search Report for Application No. 12181234.1 dated Nov. 5, 2012.

* cited by examiner

*Primary Examiner* — Navin Natnithithadha
*Assistant Examiner* — Sunita Reddy
(74) *Attorney, Agent, or Firm* — Tucker Ellis LLP

(57) ABSTRACT

A data processing method of determining a treatment plan including a corresponding program and a computer running the program. The treatment plan describes a medical treatment to be carried out on a patient and executed by a computer, including acquiring current patient data comprising current patient information about a current patient's body, and determining, based on the current patient data, reference treatment plan data comprising reference treatment plan information about a reference treatment plan.

12 Claims, 2 Drawing Sheets

AUTOMATIC TREATMENT PLANNING METHOD

RELATED APPLICATION DATA

This application claims priority of the U.S. Provisional Application No. 61/541,415 filed on Sep. 30, 2011, which is incorporated herein by reference in its entirety.

FIELD OF THE INVENTION

The present invention is directed to a method, in particular data processing method of determining a treatment plan as defined by the independent claim.

BACKGROUND

Planning a treatment, in particular a radiotherapy treatment, typically is a time-consuming and lengthy process which is normally performed by a medical physicist. This invention eliminates treatment planning as a manual process by proposing a method of automatic treatment planning and provides the advantage of adaptingR%.a predetermined treatment plan to a current anatomical situation, in particular in case new 3D anatomical information about the patient's body is available. This is in particular necessary if the precise position of for example organs in the interior of a patient's body is not known due to movement of the organs when placing the patient onto a bed for radiotherapy treatment or due for example the varying spatial extent of other organs, such as the urinary bladder which depends on the level of fluid held by the bladder. In that case, it is necessary to adapt a predetermined geometry of treatment beams to the current position of the target region (which is meant to be irradiated with the treatment beams) relative to the rest of the patient's body or to the treatment device.

OVERVIEW OF EXAMPLE EMBODIMENTS

A problem to be solved by the invention is to provide an automatic treatment planning, in particular to increase the efficiency with which a treatment plan can be generated.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

The method in accordance with the invention is in particular a data processing method. The data processing method is preferably performed using technical means, in particular a computer. In particular, the data processing method is executed by or on the computer. The computer in particular comprises a processor and a memory in order to process the data, in particular electronically and/or optically. The acquiring, determining and/or calculating steps described are in particular performed by a computer. Determining or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "subcomputers", wherein each sub-computer represents a computer in its own right. The term of computer encompasses a cloud computer, in particular a cloud server. The term of cloud computer encompasses cloud computer system in particular comprises a system of at least one cloud computer, in particular plural operatively interconnected cloud computers such as a server farm. Preferably, the cloud computer is connected to a wide area network such as the world wide web (WWW). Such a cloud computer is located in a so-called cloud of computers which are all connected to the world wide web. Such an infrastructure is used for cloud computing which describes computation, software, data access and storage services that do not require end-user knowledge of physical location and configuration of the computer that delivers a specific service. In particular, the term "cloud" is used as a metaphor for the internet (world wide web). In particular, the cloud provides computing infrastructure as a service (IaaS). The cloud computer may function as a virtual host for an operating system and/or data processing application which is used for executing the inventive method. Preferably, the cloud computer is an elastic compute cloud (EC2) provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals represent in particular the data received or outputted by the computer.

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit—CPU) which executes the computer program elements and optionally a volatile memory (in particular, a random access memory—RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electro-magnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. Preferably, the data storage medium is a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The present invention also relates to the field of controlling a treatment beam. The present invention further relates to the field of medicine and in particular to the use of beams, in particular radiation beams, to treat parts of a patient's body, which are also called treatment beams. A treatment beam treats body parts which are to be treated, which are referred to in the following as "treatment body parts". These body parts are in particular parts of a patient's body, i.e. anatomical body parts. Ionising radiation is in particular used for the purpose of treatment. In particular, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation are X-rays, high-energy particles (high-energy particle beams) and/or ionizing radiation emitted from a radioactive element. The treatment radiation, in particular the treatment beam, is in particular used in radiation therapy or radiotherapy, in particular in the field of oncology. For treating cancer in particular, parts of the body comprising a pathologic structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

With respect to background, reference is made to devices manufactured by Elekta and Varian Medical Systems.

A treatment body part can be treated by one or more treatment beams issued from one or more directions at one or more times. Thus the treatment by means of the at least one treatment beam follows a spatial pattern and a time pattern. To cover the spatial and time features of the treatment by means of the at least one treatment beam, the term "beam arrangement" is used. The beam arrangement is an arrangement of at least one treatment beam.

The beam positions describe the positions of the treatment beams of the beam arrangement. The arrangement of beam positions is called positional arrangement. A beam position is preferably defined by the beam direction and additional information which allows to assign a specific location in in particular a three-dimensional space to the treatment beam, for example information about the coordinates in a defined coordinate system. The specific location is one point on preferably a straight line. This line is called "beam line" and runs in the beam direction and for instance runs along the central axis of the treatment beam. The defined coordinate system is preferably defined relative to the treatment device or relative to at least part of the patient's body. The positional arrangement comprises (in particular consists of) at least one beam position, in particular a discrete set of beam positions (e.g. two or more different beam positions) or a continuous multiplicity (manifold) of beam positions.

During treatment, one or more treatment beams in particular adopts the treatment beam positions defined by the positional arrangement simultaneously or sequentially (the latter in particular in case there is just one beam source to emit a treatment beam). If there are several beam sources, at least a sub-set of all beam positions can also be adopted simultaneously by treatment beams during the treatment. In particular one or more sub-sets of the treatment beams can adopt the beam positions of the arrangement in accordance with a pre-defined sequence. A sub set of treatment beams comprises one or more treatment beams. The full set of treatment beams which comprise one or more treatment beams and which adopts all beam positions defined by the positional arrangement is the beam arrangement.

The movements of the treatment body parts are in particular due to movements which are referred to in the following as "vital movements". Reference is also made in this respect to the above-mentioned applications EP 08 169 422.6 and EP 09 160 153.4, which discuss these vital movements in detail. In order to determine the position of the treatment body parts, analytical devices such as x-ray devices (in particular cone beam CT—CBCT devices), CT devices or MRT devices are used to generate analytical images (such as x-ray images or MRT images) of the body. Analytical devices are in particular devices for analysing a patient's body, for instance by using waves and/or radiation and/or energy beams, in particular electromagnetic waves and/or radiation, ultrasound waves and/or particles beams. Analytical devices are in particular devices which generate images (for example, two-dimensional or three-dimensional images) of the patient's body (in particular, internal structures and/or anatomical parts of the patient's body) by analysing the body. Analytical devices are in particular used in medical diagnosis, in particular in radiology. However, it can be difficult to identify the treatment body part within the analytical image. It can in particular be easier to identify an indicator body part which correlates with changes in the position of the treatment body part and in particular the movement of the treatment body part. Thus, tracking an indicator body part allows a movement of the treatment body part to be tracked on the basis of a known correlation between the changes in the position (in particular the movements) of the indicator body part and the treatment body part.

In the field of medicine, imaging methods are used to generate image data (for example, two-dimensional or three-dimensional image data) of anatomical structures (such as soft tissues, bones, organs, etc.) of the human body. Medical imaging methods are understood to mean advantageously apparatus-based imaging methods (so-called medical imaging modalities and/or radiological imaging methods), such as for instance computed tomography (CT) and cone beam computed tomography (CBCT; in particular volumetric CBCT), x-ray tomography, magnetic resonance tomography (MRT or MRI), conventional x-ray, sonography and/or ultrasound examinations, and positron emission tomography. Analytical devices are in particular used to generate the image data in apparatus-based imaging methods. The imaging methods are in particular used for medical diagnostics, to analyse the anatomical body in order to generate images which are described by the image data. The imaging methods are in particular used to detect pathological changes in the human body. However, some of the changes in the anatomical structure, in particular the pathological changes in the structures (tissue), may not be detectable and in particular may not be visible in the images generated by the imaging methods. A tumour for example represents an example of a change in an anatomical structure. If the tumour grows, it may then be said to represent an expanded anatomical structure. This expanded anatomical structure may not be detectable; in particular, only a part of the expanded anatomical structure may be detectable. Primary/high-grade brain tumours are for example usually visible on MRI scans when contrast agents are used to infiltrate the tumour. The MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and in particular discernable in the image generated by the imaging method. In addition to these tumours, referred to as "enhancing" tumours, it is thought that approximately 10% of brain tumours are not discernable on a scan and are in particular not visible to a user looking at the images generated by the imaging method.

Preferably, the inventive method is at least partly executed by a computer. That is, all steps or just some of the steps (i.e. less than a total number of steps) of the inventive method may be executed by a computer.

The inventive method preferably is a data processing method and constitutes a method of determining a treatment plan. A treatment plan preferably describes a medical treatment to be carried out on a patient. In particular, a treatment plan comprises information about pharmaceuticals to be given to the patient, for example about the type of pharmaceuticals and the dose in which they are to be applied. In case the medical treatment to be carried out comprises treatment by radiotherapy, a treatment plan in particular comprises information about the points in time and/or the time intervals at which radiotherapy sessions are to be conducted on the patient. In the case of radiotherapy treatment, the term of dose refers to a radiation dose caused by irradiation with in particular treatment radiation. Besides that, a radiotherapy treatment plan in particular comprises information about the kind of and dose (more particularly, the energy and time length of irradiation) of radiation to be applied. Furthermore, a radiotherapy treatment plan may comprise information about the location of the target region in the patient's body and the kind of disease from which the patient is suffering (such as the kind of tumour to be irradiated). In particular, a treatment plan for radiotherapy comprises information about the relative position between the target region and an arrangement of treatment beams. In general, a treatment plan may also comprise information about the anatomy or physiology of the patient, such as information about his height and weight, his gender, age and vital parameters (such as blood pressure, breathing frequency and heart rate). A radiotherapy treatment plan in particular comprises information about the treatment beam or treatment beams to be used, in particular by the arrangement of treatment beams. More particularly, a radiotherapy treatment plan comprises information about the positional arrangement of the arrangement of treatment beams, advantageously the position of the positional arrangement relative to the patient's body (in particular, relative to the target region, relative to healthy tissue or relative to critical structures). Preferably, the position of each beam line relative to the patient's body (or the aforementioned parts of the patient's body) is described by information contained in the treatment plan. Information describing the geometric relationship (i.e. the position or the positional arrangement relative to the patient's body and the positional arrangement itself) is in the framework of this disclosure also called patient-beam-relationship information.

Preferably, current patient data comprising current patient information about a current patient's body is acquired. The current patient preferably is the patient on which the medical treatment described by the treatment plan is to be carried out. The treatment plan is thus also called a current treatment plan. The current patient information preferably comprises categories of information which describe medical information about the current patient. In particular, the medical information relates to anatomical, physiological or pathological information (also called current patient medical information) about the current patient. For example, the medical information describes the current patient's body dimensions (such as height or the geometry of specific body parts) or physiological parameters of the current patient's body (such as average blood pressure, heart rate or breathing rate) or pathological information (such as information about the patient's medical history or information about an illness or injury from which the current patient is suffering).

Preferably, reference treatment plan data comprising reference treatment plan information about a reference treatment plan is determined based on the current patient data. Preferably, the reference treatment plan has been drafted for patient data which fulfill specific conditions with respect to the current patient data. These conditions are described further below. Preferably, the reference treatment plan is predetermined and has been drafted to suit a medical treatment to be carried out on a reference patient. Information about the reference patient's body is preferably described by reference patient data and the reference treatment plan information has been generated preferably based on the reference patient data. The current patient and the reference patient may in a particular embodiment of the invention be identical which means that the current treatment plan is determined on a reference treatment plan which has also been generated for treatment of the current patient. This has the advantage that the medical history of the current patient can be used to determine the current treatment plan which may in some cases lead to a more patient-specific medical treatment. The reference treatment plan data is preferably stored as predetermined data in a database and comprises categories of information which comprise at least the categories of information described above with regard to the treatment plan in general.

Preferably, the current patient data comprises current target region data comprising current target region information about a target region in the current patient's body. The target region preferably is a treatment body part, i.e. a part of the patient's body which is envisaged to be treated by the medical treatment, in particular by the treatment beam. Other regions of the patient's body which in particular are not part of a target region are healthy regions (healthy tissue) and critical regions (critical tissue). Healthy regions are commonly not to be treated by the medical treatment, however, an influence of the medical treatment on them is mostly inevitable but undesired. This may for example be the case if the treatment has passed through healthy tissue on its way to the target region. Critical regions are such regions which shall not be influenced by the medical treatment. In particular, an influence of the medical treatment on critical regions has to be avoided. Examples of critical structures are vital organs such as the heart which shall not be influenced by specific pharmaceuticals or functional regions of the brain which shall not be irradiated by a treatment beam in order to avoid neurological effects caused by the medical treatment.

The current target region information in particular comprises categories of information which relate to the geometry, position or pathologic state of the target region. The term of geometry in this context encompasses for example the shape (for example similarity to a basic geometric shape such as a sphere or a box) or dimension (length, diameter, radius or circumference) of the target region. The position of the target region is in particular described by its position relative to other parts of the patient's body or relative to the treatment device in the context of this disclosure, a treatment device is the device used for emitting the treatment beam such as an x-ray tube, particle accelerator or radioactive substance. The pathologic state of the target region is in particular described by the kind of disease (more particularly, the type of tumour) or injury which is present in the target region. Additionally, the pathologic state may be described by the history of the disease or injury such as the geometry or the position of the target region at a previous point in time. The geometry of a target region may also be described by the volume or the two-dimensional area (both volume and area are also referred to as size) covered by the target region in a cross section or specific perspective.

Preferably, current treatment plan data is acquired by adapting the reference treatment plan data to the current patient data. The current treatment plan data preferably comprises current treatment plan information about the medical treatment to be carried out on the current patient. The current treatment plan information in particular is treatment plan information as described above in general with regard to a treatment plan. In particular, the reference treatment plan serves as a basis for generating the current treatment plan data. More particularly, the reference treatment plan information is adapted to the requirements of treating the current patient in view of the current patient information, in particular in view of anatomical and pathological information contained in the current patient information. Adapting the reference treatment plan information in particular comprises changing the reference treatment plan information such that a treatment plan is generated which is suitable to treat the current patient with the desired medical treatment.

Preferably, reference patient data comprising reference patient information about the reference patient's body is acquired. The reference patient information comprises categories of information selected at least from the above-described categories of information which may be contained in the current patient information. Preferably, the reference patient data comprises information, preferably image information, about the geometry of at least part of the reference patient's body. Preferably, the reference patient is the patient for whom the reference patient data and the reference treatment plan data have been generated. In particular, the reference treatment plan comprises information about a medical treatment to be carried out on the reference patient.

Preferably, the reference patient data comprises information, in particular image information, about the geometry of at least part of the reference patient's body. The respective image information is hereinforth also called reference patient image information (contained in reference patient image data) and current patient image information (contained in current patient image data). The reference patient image data and current patient image data are preferably acquired by application of a medical imaging method. The medical imaging method is in particular applied to the reference patient's body in order to acquire the reference patient image data and the current patient image data, respectively. Applying the medical imaging method in particular comprises acquiring image information which represents a cone beam computed tomography (CBCT) of at least part of the current patient's body and the reference patient's body, respectively.

Preferably, the reference patient data comprises reference target region data comprising reference target region information about a reference target region in the reference patient's body. The reference target region information describes categories of information in analogy to those described by the current target region information, however with regard to the reference patient's body if applicable.

Preferably, applicability data is determined based on the current patient data and the reference patient data. The applicability data preferably comprises applicability information about the applicability of the information contained in the reference patient data to the information contained in the current patient data. In the context of this disclosure, applicability in particular means the suitability of the information contained in the reference patient data with regard to the information contained in the current patient data in view of medical aspects. In particular, the applicability information describes a degree of similarity between the information contained in the reference patient data and information contained in the current patient data. In particular, the applicability data comprises or is determined based on information about whether or not the information contained in the reference patient data is applicable to the information contained in the current patient data. The degree of similarity between the information in the reference patient data and the information in the current patient data is preferably determined based on information about a measure of similarity, in particular a correlation, between the information in the reference patient data and the information in the current patient data. The applicability information preferably comprises information about the measure of similarity, in particular the applicability information is the measure of similarity.

Preferably, the applicability data is determined based on information about the position of critical structures in the current patient's body when compared with information about the position of such critical structures in the reference patient's body. Depending on the distance between the respective positions, the measure of similarity on which the applicability information may be based can be determined. In particular, the position of the critical structure may be evaluated as a position relative to the current target region or the reference target region, respectively.

Preferably, the reference patient data is acquired based on assessing the result of elastically fusing geometry information about the geometry of at least part of the reference patient's body (also called reference patient geometry information) contained in the reference patient data to geometry information about the geometry of at least part of the current patient's body (also called current patient geometry information) contained in the current patient data. In particular, the reference patient data is acquired by elastically fusing the geometry information about the geometry of at least part of a plurality of reference patient's bodies contained in the corresponding plurality of reference patient datasets (which may be acquired within the disclosed method) to the geometry information about the geometry of at least part of the current patient's body. The parts of the respective bodies advantageously are the same anatomical structures. Then, a degree of fit of the fused reference patient geometry information fused to the current patient geometry information (also called fused geometry information) is determined. Depending on the degree of fit, i.e. the better the fit is and the smaller the differences are between the fused geometry information and the current patient geometry information, the reference patient data from which the reference patient geometry information has been acquired may be selected as the reference patient data to be used for the further steps of the method.

According to a preferable, more general embodiment, the applicability information comprises information about a geometric transformation between the current patient information and the reference patient information. In this case, the current patient information and the reference patient information in particular comprise geometric information about the anatomy of the current patient and the reference patient. The geometric transformation in particular is or comprises an elastic fusion and/or elastic fusion algorithm.

In this application, the term "image morphing" is also used as an alternative to the term "image fusion", but with the same meaning.

Elastic fusion transformations (e.g. image fusion transformation) are in particular designed to enable a seamless transition from one data set (e.g. first data set, e.g. first image) to another data set (e.g. second data set, e.g. second image). The transformation is in particular designed such that one of the first and second data sets (images) is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are in particular vectors of a deformation field F. These vectors are determined by the optimisation algorithm which results in an optimum degree of similarity. Thus, the optimum degree of similarity represents a condition, in particular a constraint, for the optimisation algorithm. The bases of the vectors lie in particular at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), in particular in order to avoid pathological deformations (for instance, all the voxels being shifted to the same position by the transformation). The constraints include in particular the constraint that the transformation is regular, which in particular means that a Jacobian determinant calculated from a matrix of the deformation field (in particular, the vector field) is larger than zero. The constraints include in particular the constraint that the transformed (deformed) image is not self-intersecting and in particular that the transformed (deformed) image does not comprise faults and/or ruptures. The constraints include in particular the constraint that if a regular grid is transformed simultaneously with the image and in a corresponding manner, the grid is not allowed to interfold at any of its locations. The optimising problem is in particular solved iteratively, in particular by means of an optimisation algorithm which is in particular a first-order optimisation algorithm, in particular a gradient descent algorithm. Other examples of optimisation algorithms include optimisation algorithms which do not use derivations such as the downhill simplex algorithm or algorithms which use higher-order derivatives such as Newton-like algorithms. The optimisation algorithm preferably performs a local optimisation. If there are a plurality of local optima, global algorithms such as simulated annealing or genetic algorithms can be used. In the case of linear optimisation problems, the simplex method can for instance be used.

In the steps of the optimisation algorithms, the voxels are in particular shifted by a magnitude in a direction such that the degree of similarity is increased. This magnitude is preferably less than a predefined limit, for instance less than $1/10$ or $1/100$ or $1/1000$ of the diameter of the image, and in particular about equal to or less than the distance between neighbouring voxels. Due in particular to a high number of (iteration) steps, large deformations can be implemented.

The determined elastic fusion transformation can be in particular used to determine a degree of similarity (similarity measure also referred to as "measure of similarity") between the first and second data set (first and second image). To this end, the deviation of the elastic fusion transformation and an identity transformation is determined. The degree of deviations can be for instance calculated by determining the difference between the determinant of the elastic fusion transformation and the identity transformation. The higher the deviation is the less is the similarity. Thus, the degree of deviation can be used to determine a measure of similarity.

A measure of similarity can in particular be determined on the basis of a determined correlation between the first and second data set.

Preferably, the current treatment plan data is determined based on the applicability data. For example, if the applicability information indicates that the reference treatment plan already fulfills the requirements for medical treatment of the current patient to a predetermined degree, the reference treatment plan data may be selected directly as the current treatment plan data without the need of further adaptation. If, however, the applicability information indicates a degree of similarity between the information contained in the reference patient data and the information in the current patient data, there will most likely exist a need of adaptation of the reference treatment plan information. In that case, determining the current treatment plan data preferably comprises adapting the reference treatment plan data based on the applicability data. The applicability data thus preferably also comprises information about how to adapt the reference treatment plan data in view of the medical treatment to be carried out on the current patient. Preferably, adapting the reference treatment plan data comprises applying a geometric transformation such as an elastic fusion algorithm to the reference treatment plan data. In particular, information about a positional arrangement or an arrangement of treatment beams described by the reference treatment plan information is elastically fused to the current patient geometry information.

Further preferably, the reference patient data comprises reference medical information in particular about the reference patient. The respective medical information preferably comprises at least one of anatomical, physiological and pathological information with regard to the respective patient as defined further above with regard to the current patient medical information.

Preferably, the current treatment plan data is determined by computing it on a cloud server. In particular, the reference treatment plan data is downloaded from a cloud server, for example to a local client computer. As part of adapting the reference treatment plan information, transformation data is then determined at the client computer, the transformation data comprising transformation information about the transformation from the reference treatment plan information to the current treatment plan information. Instead of computing the current treatment plan data at the client computer and uploading the correspondingly large amount of information to a cloud server, preferably only the transformation data is uploaded from the client computer to the cloud server in order to reduce data traffic between the two computers. The cloud server then uses the transformation information to adapt the reference treatment plan data which is still stored in the cloud. This allows use of the large computational capacities of a cloud server for conducting the computation of the expensive computation of the current treatment plan data.

Preferably, the transformation information describes a difference between the reference treatment plan information and the current treatment plan information. For example, the transformation information may describe only elements of the reference treatment plan information which may not be applied for conducting the medical treatment on the current patient. In particular, the transformation information describes a distortion embodied by a matrix transformation between the positional arrangement described by the reference treatment plan information and a positional arrangement to be described by the current treatment plan information, in particular a positional arrangement which has to be computed in order for the medical treatment to be feasible with regard to the current patient's needs. The transformation data is preferably determined based on the current patient data and the reference treatment plan data.

Preferably, the aforementioned current patient image data is acquired after the current patient has been put in place for medical treatment, in particular after the current patient has been placed on a bed on which he normally rests during radiotherapy. In particular, the current patient image data is acquired immediately before the medical treatment starts, in particular immediately before radiotherapy ensues.

The aforementioned measure of similarity described by the applicability information according to a preferred embodiment describes a similarity between the geometry of the current target region and the geometry of the reference target region. The term of geometry encompasses the same terminology as defined above with regard to the geometry of the current target region. In particular, the measure of similarity may in this case be acquired based on applying a three-dimensional subtraction algorithm with geometry information about the geometry of the current target region and geometry information about the geometry of the reference target region as inputs. Thereby, a difference between the two geometries, in particular a greater volume of one of the two target regions compared to the other one of the two target regions, can be determined. A subtraction algorithm essentially places predefined parts of image information over one another and outputs the difference or differences between the sets of image information (which are used as an input) with regard to one another.

Preferably, and in case the current patient is the reference patient, it is not necessary to determine the reference treatment plan data based on the reference patient data. Rather, the reference treatment plan data may be selected directly by a user who has knowledge of reference treatment plan data which has been generated specifically for treatment of the current patient. In case the current patient is the reference patient (i.e. is identical in person to the reference patient), the determined or selected reference treatment plan information in particular comprises information about the medical treatment previously applied to the current patient.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

Preferably, the computer on which the aforementioned program is running is or comprises a cloud server.

The invention also encompasses a radiotherapy system comprising the aforementioned computer and a treatment device for treating a treatment body part of the current patient.

The treatment device in particular comprises a treatment beam source for emitting a treatment beam. Furthermore, the radiotherapy system preferably comprises a beam source driver for changing the position of the treatment beam source. The beam source driver may for example comprise a motor and a mechanism which supports movement of the treatment beam source, in particular relative to the position of the patient (alternatively or additionally, the treatment beam source driver may be configured to move the patient relative to the position of the beam source).

The radiotherapy system preferably also comprises an analytical device constituted to generate at least one x-ray image of the current patient prior to applying the medical treatment to the patient. As mentioned before, the analytical device preferably comprises a CBCT device.

In order to verify that the current treatment plan information in fact is suitable for conducting the envisaged medical treatment on the current patient, the method described herein may also comprise steps of approving of the current treatment plan information. These steps are contained in the following further advantageous embodiments A to G which may be combined without prejudice with the above-described method of determining a treatment plan:

A. A method, in particular data processing method, of advantageously automatically approving of a treatment plan which describes a medical treatment to be carried out on a patient, the steps of the method being executed by a computer and comprising:
acquiring approval template data comprising approval template information that describes an approval template containing acceptance and advantageously rejection criteria for current treatment plan information;
determining criteria fulfillment data comprising criteria fulfillment information describing whether the current treatment plan information fulfils the criteria described by the approval template information or not; and
accepting the current treatment plan information for carrying out the medical treatment on the patient if the criteria fulfillment information indicates that the current treatment plan information fulfils the criteria described by the approval template information, otherwise rejecting the current treatment plan information for further use in the medical treatment.

B. The method according to embodiment A, wherein the approval template information include information about a conformity index and/or a homogeneity index.

The term of conformity index describes a measure of how much of a projected surface or cross-section of the current target volume is covered by a treatment plan. The term of homogeneity index describes a measure of how (homogeneously) a dose applied to healthy tissue and critical structures is distributed over the patient's body or the respective healthy tissue and critical structures.

C. The method according to any one of embodiments A or B, wherein the approval template information includes information about a minimum dose to be applied to the current target region.

D. The method according to any one of embodiments A to C, wherein the approval template information includes information about a maximum dose to be applied to critical structures.

E. The method according to any one of embodiments A to D, wherein the approval template information includes information about a predetermined amount by which a dose distribution achieved when adapting geometry information about critical structures and the reference target volume to geometry information in the current patient data, may differ from a predefined dose distribution.

F. The method according to any one of embodiments A to E, wherein the approval template information comprises information about a predetermined threshold value by which a distortion of a positional arrangement of treatment beams caused by adapting information about the positional arrangement contained in the reference treatment plan information to geometry information contained in the current patient information may not exceed.

G. The method according to any one of embodiments A to F, wherein the approval template information is set independently for a minimum dose to be reached in the current target volume, a maximum dose to be reached in the target volume and a maximum dose to be reached in a critical structure.

BRIEF DESCRIPTION OF THE DRAWINGS

In the following, example embodiments of the present invention are described with reference to the figures, which are merely to be regarded as examples of the invention without limiting the invention to these specific embodiments, wherein.

DESCRIPTION OF EXAMPLE EMBODIMENTS

Figure 1:
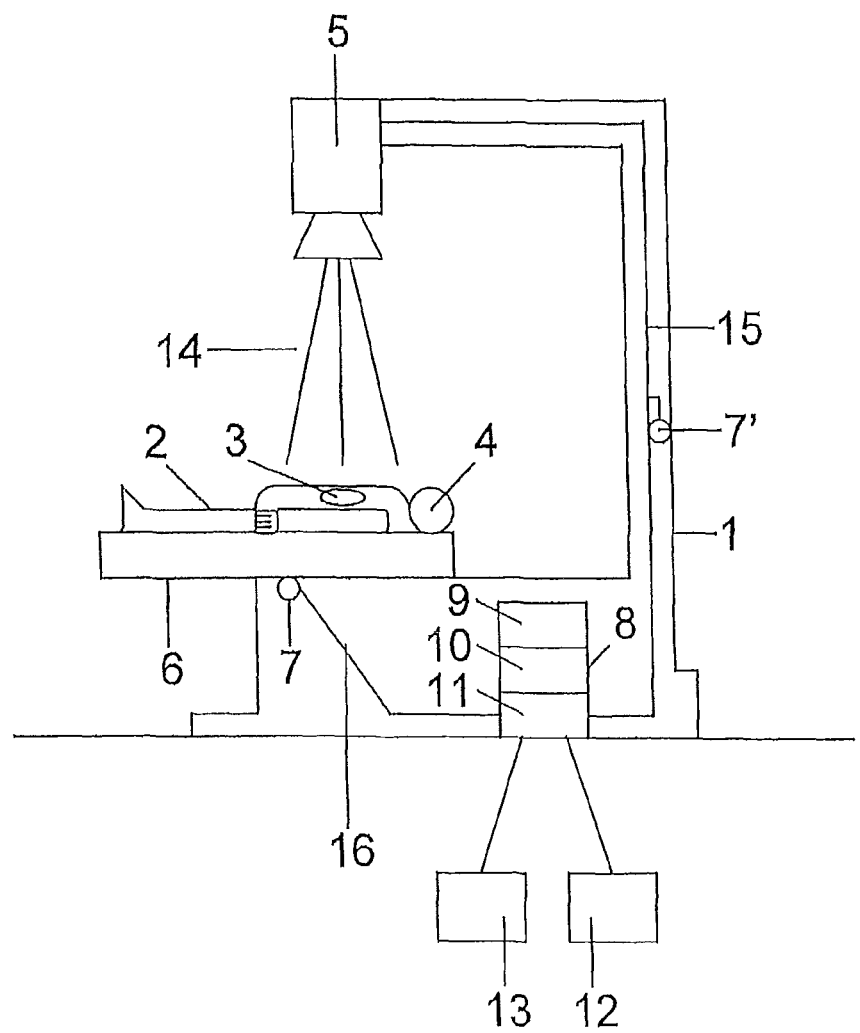
FIG. 1 shows a treatment setup as an example of a radiotherapy system with a patient's body placed ready for treatment by a treatment device.

As shown in FIG. 1, a patient's body 2 comprising a target region 3 and an off-target region 4 is placed on a patient couch 6 of a treatment device 1. The off-target region 4 comprises for example healthy tissue. The treatment device 1 comprises an irradiation portion 5 which is configured to take a CBCT image of the patient's body and to emit the treatment radiation 14. The treatment device 1 also comprises a motor 7 which is coupled to a transport mechanism of the couch 6 in order to move the patient's body 2 after it has been placed on the couch 6. The treatment device 1 also includes a computer 8 comprising a hard disc 9, a RAM 10 and a CPU 11. The computer 8 is connected by a data line 15 to the irradiation portion 5. The computer 8 is also connected to an input portion 13 and a display unit 12. The input portion 13 preferably comprises a keyboard and a pointing device such as a mouse or a joystick. The display unit 12 preferably comprises a graphic display device such as a monitor and an acoustic output device such as a loudspeaker. The computer 8 is also connected to the electric motor 7 via a data line 16 in order to automatically control the electric motor 7 in moving the couch 6. The treatment device 1 also comprises another electric motor 7' which is also connected to the computer 8 by the data line 15 and is designed to move, in particular shift and/or rotate, the irradiation portion 5 in an absolute co-ordinate system. The electric motor 7' can in particular move the irradiation portion 5 relative to the base of the treatment device 1 and/or relative to the absolute position of the couch 6 and therefore the patient's body 2 if it is placed on the couch 6. Furthermore, the treatment device 1 is configured to vary other parameters of the beam, in particular the beam geometry (the shape of the beam), the number of beams, or the beam intensity.

The computer 8 is configured to execute the data processing method as described above by running the above-mentioned program.

Figure 2:
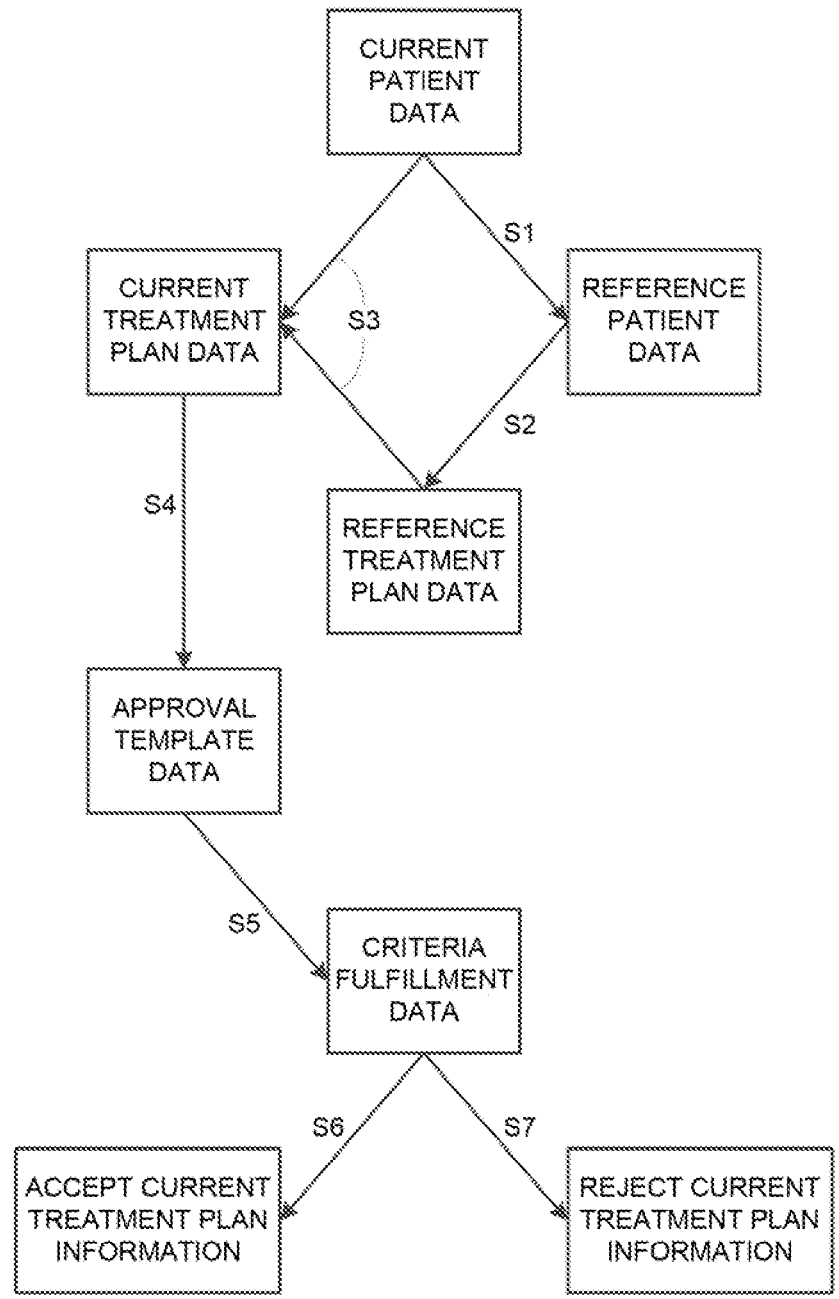
FIG. 2 is a flow diagram of an embodiment of the present invention.

FIG. 2 shows a flow diagram of a specific embodiment of the inventive method. After starting the method, the current patient data is acquired. In step S1, reference patient data which fulfills the above-described criteria of applicability to the current patient data is acquired. Based on the knowledge about the reference patient for whom the reference patient data was generated, step S2 continues with acquiring the reference treatment plan data. The reference treatment plan data is adapted to geometry information contained in the current patient data in order to determine the current treatment plan data in step S3. In step S4, the approval template data is acquired and step S5 continues with comparing the current treatment plan information to the approval template information contained in the approval template data. The result of the comparison is output as criteria fulfillment data. If the comparison results in that the acceptance criteria of the approval template information are fulfilled, the current treatment plan information is accepted in step S6. If it is concluded that the current treatment plan information does not fulfill the fulfillment criteria or fulfills rejection criteria (if the latter are contained in the approval template information), the current treatment plan information is rejected in step S7. In that case, the inventive method may return to its start and for a new run of the search for reference patient data which fulfill the applicability criteria described above in the manner next best to the manner in which the reference patient data previously acquired fulfilled the applicability criteria.

If the fulfillment criteria information comprises information about minimum or maximum dose values to be achieved, for example, in the current target region, a simulation of a radiotherapy session based on the current treatment plan information and the current patient information may provide image data from which an absorption coefficient in specific tissue of the patient's body may be determined, in particular by using the concept of Hounsfield units. Thereby, it may be determined whether the radiation therapy parameters contained in the current treatment plan information are acceptable in view of the dose parameters described by the approval template information.

In particular, the invention further relates to the following embodiments which are parts of the description. Advantageous features of the different embodiments can be combined with each other in one embodiment. It is further possible to omit one or more features from a specific embodiment. The omitted one or more features are not necessary for the specific embodiment.

Preferred embodiments and/or features of the invention are indicated as follows:

H. A data processing method of determining a treatment plan, the treatment plan describing a medical treatment to be carried out on a patient, the steps of the method being executed by a computer and comprising:
  a) acquiring current patient data comprising current patient information about a current patient's body;
  b) determining, based on the current patient data, reference treatment plan data comprising reference treatment plan information about a reference treatment plan.

I. The method according to the preceding embodiment, wherein the current patient data comprises current target region data comprising current target region information about a current target region in the current patient's body.

J. The method according to any one of the preceding embodiments, comprising:
  acquiring, based on the current patient data, current treatment plan data comprising current treatment plan information about a medical treatment to be carried out on the current patient.

K. The method according to the preceding embodiment, wherein acquiring the current treatment plan data comprises adapting the reference treatment plan data based on the current patient data or selecting the reference treatment plan data as current treatment plan data.

L. The method according to any one of the preceding embodiments, comprising:
  acquiring reference patient data comprising reference patient information about a reference patient's body.

M. The method according to the preceding embodiment, wherein the reference patient data comprises information, preferably image information, about the geometry of at least part of the reference patient's body and wherein the current patient data comprises information, preferably image information, about the geometry of at least part of the current patient's body.

N. The method according to the preceding embodiment, wherein the reference patient data comprises reference target region data comprising reference target region information about a reference target region in the reference patient's body.

O. The method according to any one of the preceding embodiments as far as dependent on embodiment no. E, comprising:
  determining, based on the current patient data and the reference patient data, applicability data comprising applicability information about the applicability of the information contained in the reference patient data to the information contained in the current patient data.

P. The method according to the preceding embodiment, wherein the applicability data comprises or is determined based on information about whether or not the information contained in the reference patient data is applicable to the information contained in the current patient data.

Q. The method according to any one of the two preceding embodiments, wherein the applicability data is information about a measure of similarity, in particular a correlation, between information in the reference patient data and information in the current patient data or is determined based on the information about a measure of similarity.

R. The method according to any one of the preceding embodiments, wherein the reference patient data is acquired based on assessing the result of elastically fusing geometry information about the geometry of at least part of the reference patient's body contained in the reference patient data to geometry information about the geometry of at least part of the current patient's body contained in the current patient data.

S. The method according to any one of the four preceding embodiments, wherein the applicability data is determined based on information about the position of critical structures in the current patient body, in particular, and as far as the method is dependent on embodiment no. B and embodiment no. G, relative to the current target region, or in the reference patient body, in particular, and as far as the method is dependent on embodiment no. B and embodiment no. E, relative to the reference target region.

T. The method according to any one of the five preceding embodiments, wherein the applicability information comprises information about a geometric transformation, in particular an elastic fusion, between the current patient information and the reference patient information.

U. The method according to the preceding embodiment as far as dependent on embodiment J, wherein the current treatment plan data is determined based on the applicability data.

V. The method according to the preceding embodiment, wherein determining the current treatment plan data comprises adapting the reference treatment plan data based on the applicability data.

W. The method according to any one of the preceding embodiments as far as dependent on embodiment J, wherein the current target region data comprises information about spatial characteristics of the current target region, in particular the geometry or position of the current target region.

X. The method according to any one of the preceding embodiments, wherein the current patient data comprises current patient medical information about the current patient and wherein the reference patient data comprises reference medical information in particular about the reference patient.

Y. The method according to the preceding embodiment, wherein the medical information comprises anatomical, physiological or pathological information.

Z. The method according to any one of the preceding embodiments, wherein the medical treatment comprises treatment by radiotherapy.

AA. The method according to the preceding embodiment as far as dependent on embodiment V, wherein adapting the reference treatment plan data comprises applying an elastic fusion algorithm to the reference treatment plan data.

BB. The method according to any one of the two preceding embodiments, wherein the reference treatment plan data comprises information about a positional arrangement of treatment beams and wherein adapting the reference treatment plan comprises changing the positional arrangement of an arrangement of treatment beams described by the reference treatment plan information based on applying an elastic fusion algorithm to the reference treatment plan data.

CC. The method according to embodiment AA, wherein current treatment plan data is determined by computing it on a cloud server, wherein the reference treatment plan data is downloaded from a cloud server and transformation data comprising transformation information about a transformation from the reference treatment plan information to the current treatment plan information is uploaded to the cloud server for computation of the current treatment plan data.

DD. The method according to the preceding embodiment, wherein the transformation information describes a difference between the reference treatment plan information and the current treatment plan information.

EE. The method according to the preceding claim as far as dependent on embodiment BB, wherein the transformation information describes a distortion matrix between the positional arrangement described by the reference treatment plan information and a positional arrangement to be described by the current treatment plan information.

FF. The method according to any one of the preceding embodiments, wherein the current patient data comprises current patient image data and wherein the reference patient data comprises reference patient image data, the current patient image data and the reference patient image data acquired by application of a medical imaging method.

GG. The method according to the preceding embodiment, wherein the application of a medical imaging method comprises acquiring image information representing a cone beam computed tomography of at least part of the current patient's body and the reference patient's body.

HH. The method according to the preceding embodiment, wherein the current patient image data is acquired after the current patient has been put in place for medical treatment, in particular immediately before the medical treatment starts.

II. The method according to any one of the preceding embodiments as far as dependent on embodiment I and embodiment N, wherein the applicability data comprises information about a measure of similarity between the geometry of the current target region and the geometry of the reference target region.

JJ. The method according to the preceding embodiment, wherein the measure of similarity is acquired based on applying a three-dimensional subtraction algorithm.

KK. The method according to any one of the preceding embodiments as far as dependent on embodiment M, wherein the current patient is the reference patient.

LL. The method according to the preceding embodiment, wherein the reference treatment plan data has been generated specifically for treatment of the current patient, wherein the reference treatment plan information in particular comprises information about a medical treatment previously applied to the current patient.

MM. The method according to any one of embodiments J to LL, comprising:
  acquiring approval template data comprising approval template information that describes an approval template containing acceptance and advantageously rejection criteria for current treatment plan information;
  determining criteria fulfillment data comprising criteria fulfillment information describing whether the current treatment plan information fulfils the criteria described by the approval template information or not; and
  accepting the current treatment plan information for carrying out the medical treatment on the patient if the criteria fulfillment information indicates that the current treatment plan information fulfils the criteria described by the approval template information, otherwise rejecting the current treatment plan information for further use in the medical treatment.

NN. A program which, when running on a computer or when loaded onto a computer, causes the computer to perform one or more or all of the method steps according to any one of the preceding claims and/or a program storage medium on which the program is stored in particular in a non-transitory form and/or a computer on which the program is running or into the memory of which the program is loaded and/or a signal wave, in particular a digital signal wave, carrying information which represents the program, in particular the aforementioned program, which in particular comprises code means which are adapted to perform any or all of the method steps described herein.

OO. The computer according to the preceding embodiment, wherein the computer comprises a cloud server.

PP. A radiotherapy system, comprising:
  the computer according to any one of the two preceding embodiments;
  a treatment device for treating a treatment body part of the current patient, the treatment device comprising a treatment beam source.

QQ. The radiotherapy system according to the preceding embodiment, comprising:
  a beam source driver for changing the position of the treatment beam source.

RR. The radiotherapy system according to any one of the two preceding embodiments, comprising:
  an analytical device constituted to generate at least one x-ray image of the current patient prior to applying the medical treatment to the current patient.

SS. The radiotherapy system according to the preceding claim, wherein the analytical device is a CBCT device.

TT. A method, in particular data processing method, of advantageously automatically approving of a treatment plan which describes a medical treatment to be carried out on a patient, the steps of the method being executed by a computer and comprising:

acquiring approval template data comprising approval template information that describes an approval template containing acceptance and advantageously rejection criteria for current treatment plan information;

determining criteria fulfillment data comprising criteria fulfillment information describing whether the current treatment plan information fulfils the criteria described by the approval template information or not; and accepting the current treatment plan information for carrying out the medical treatment on the patient if the criteria fulfillment information indicates that the current treatment plan information fulfils the criteria described by the approval template information, otherwise rejecting the current treatment plan information for further use in the medical treatment.

UU. The method according to the preceding embodiments, wherein the approval template information include information about a conformity index and/or a homogeneity index.

VV. The method according to any one of the two preceding embodiments, the approval template information includes information about a minimum dose to be applied to the current target region.

WW. The method according to any one of the three preceding embodiments, wherein the approval template information includes information about a maximum dose to be applied to critical structures.

XX. The method according to any one of the four preceding embodiments, wherein the approval template information includes information about a predetermined amount by which a dose distribution achieved when adapting geometry information about critical structures and the reference target volume to geometry information in the current patient data, may differ from a predefined dose distribution.

YY. The method according to any one of the preceding five embodiments, wherein the approval template information comprises information about a predetermined threshold value by which a distortion of a positional arrangement of treatment beams caused by adapting information about the positional arrangement contained in the reference treatment plan information to geometry information contained in the current patient information may not exceed.

ZZ. The method according to any one of the preceding six embodiments, wherein the approval template information is set independently for a minimum dose to be reached in the current target volume, a maximum dose to be reached in the target volume and a maximum dose to be reached in a critical structure.

The invention claimed is:

1. A data processing method of determining a treatment plan describing a medical treatment to be carried out on a body of a current associated patient, the steps of the method being executed by a computer and comprising:

a. acquiring current patient data comprising image information about a geometry of the body of the current associated patient;

b. acquiring, based on the current patient data, reference patient data comprising image information about a geometry of a body of a reference patient;

c. determining, based on the current patient data and the reference patient data, applicability data comprising applicability information about an applicability of the image information contained in the reference patient data to the image information contained in the current patient data;

d. acquiring, based on the reference patient data and the applicability data, reference treatment plan data comprising reference treatment plan information about a reference treatment plan;

e. determining, based on the current patient data and the reference treatment plan data, current treatment plan data comprising current treatment plan information about the medical treatment to be carried out on the current associated patient;

f. adapting the reference treatment plan data in accordance with the current patient data; and g. determining the current treatment plan data based on adapting the reference treatment plan data in accordance with the current patient data, wherein the acquiring reference patient data based on the current patient data further comprises:

creating a plurality of fused geometry information by elastically fusing geometry information about the geometry of at least part of a plurality of reference patient's bodies contained in a corresponding plurality of reference patient datasets to geometry information about the geometry of at least part of the current associated patient's body, wherein the parts of the respective bodies are of corresponding anatomical structures;

determining a degree of fit of each of the plurality of fused geometry reformation, wherein the degree of fit is inversely proportional to a difference between the fused geometry reformation and the current patient geometry information; and, selecting the reference patient dataset associated with the fused geometry information with a highest degree of fit as the reference patient data.

2. The method according to claim 1, wherein the current patient data comprises current target region data comprising current target region information about a current target region in the body of the current associated patient.

3. The method according to claim 1, wherein:

the applicability data comprises information about a measure of correlation between selected reference patient information in the reference patient data and selected current patient information in the current patient data and is determined based on the information about the measure of correlation.

4. The method according to claim 1, wherein the current patient data comprises current target region data comprising current target region information about a current target region in the body of the current associated patient; and wherein the applicability data is determined based on one or more of:

information about a position of a critical structure in the body of the current associated patient relative to the current target region, or a position of a critical structure in the body of the reference patient relative to a reference target region.

5. The method according to claim 1, wherein the applicability information comprises information about a geometric transformation, the information about the geometric transformation selectively comprising information about an elastic fusion between the current patient information and the reference patient information.

6. The method according to claim 5, wherein the current treatment plan data is acquired based on the applicability data.

7. The method according to claim 6, wherein determining the current treatment plan data comprises adapting the reference treatment plan data based on the applicability data.

8. The method according to claim 1, wherein the current patient data comprises current patient image data and wherein the reference patient data comprises reference patient image data, the method further comprising acquiring the current patient image data and the reference patient image data by application of a medical imaging method.

9. The method according to claim 8, wherein the application of the medical imaging method comprises acquiring image information representing a cone beam computed tomography of at least part of the body of the current associated patient and the body of the reference patient.

10. The method according to claim 1, further comprising:
acquiring approval template data comprising approval template information that describes an approval template containing acceptance criteria for the current treatment plan information and rejection criteria for the current treatment plan information;
determining criteria fulfillment data comprising criteria fulfillment information describing whether the current treatment plan information fulfils the criteria described by the approval template information; and
accepting the current treatment plan information for selectively carrying out the medical treatment on the current patient if the criteria fulfillment information indicates that the current treatment plan information fulfils the criteria described by the approval template information, and selectively rejecting the current treatment plan information for further use in the medical treatment if the criteria fulfillment information indicates that the current treatment plan information does not fulfil the criteria described by the approval template information.

11. A non-transitory computer readable storage medium wherein code embodied in the computer readable storage medium executed by a processor performs operations, the operations comprising:
a. acquiring, by the computer, current patient data comprising image information about a geometry of the body of the current associated patient;
b. acquiring, by the computer and based on the current patient data, reference patient data comprising image information about a geometry of a body of a reference patient;
c. determining, by the computer and based on the current patient data and the reference patient data, applicability data comprising applicability information about an applicability of the image information contained in the reference patient data to the image information contained in the current patient data;
d. acquiring, by the computer and based on the reference patient data and the applicability data, reference treatment plan data comprising reference treatment plan information about a reference treatment plan;
e. determining, by the computer and based on the current patient data and the reference treatment plan data, current treatment plan data comprising current treatment plan information about the medical treatment to be carried out on the current patient;
f. adapting the reference treatment plan data in accordance with the current patient data; and
g. determining the current treatment plan data based on adapting the reference treatment plan data in accordance with the current patient data,
wherein the acquiring reference patient data based on the current patient data further comprises:
creating a plurality of fused geometry information by elastically fusing geometry information about the geometry of at least part of a plurality of reference patient's bodies contained in a corresponding plurality of reference patient datasets to geometry information about the geometry of at least part of the current associated patient's body, wherein the parts of the respective bodies are of corresponding anatomical structures;
determining a degree of fit of each of the plurality of fused geometry reformation, wherein the degree of fit is inversely proportional to a difference between the fused geometry reformation and the current patient geometry information; and,
selecting the reference patient dataset associated with the fused geometry information with a highest degree of fit as the reference patient data.

12. A radiotherapy system for determining a treatment plan describing a medical treatment to be carried out on a body of a current associated patient, the radiotherapy system comprising:
a treatment device adapted for treating a treatment body part of a current associated patient, the treatment device comprising a treatment beam source; and
a computer comprising a processor configured to:
a. acquire current patient data comprising image information about a geometry of the body of the current associated patient;
b. acquire, based on the current patient data, reference patient data comprising image information about a geometry of a body of a reference patient;
c. determine, based on the current patient data and the reference patient data, applicability data comprising applicability information about an applicability of the image information contained in the reference patient data to the image information contained in the current patient data;
d. acquire, based on the reference patient data and the applicability data, reference treatment plan data comprising reference treatment plan information about a reference treatment plan;
e. determine, based on the current patient data and the reference treatment plan data, current treatment plan data comprising current treatment plan information about the medical treatment to be carried out on the current associated patient;
f. adapting the reference treatment plan data in accordance with the current patient data; and
g. determining the current treatment plan data based on adapting the reference treatment plan data in accordance with the current patient data,
wherein the acquiring reference patient data based on the current patient data further comprises:
creating a plurality of fused geometry information by elastically fusing geometry information about the geometry of at least part of a plurality of reference patient's bodies contained in a corresponding plurality of reference patient datasets to geometry information about the geometry of at least part of the current associated patient's body, wherein the parts of the respective bodies are of corresponding anatomical structures;

determining a degree of fit of each of the plurality of fused geometry reformation, wherein the degree of fit is inversely proportional to a difference between the fused geometry reformation and the current patient geometry information; and, selecting the reference patient dataset associated with the fused geometry information with a highest degree of fit as the reference patient data.

* * * * *